(12) United States Patent
Miriuka et al.

(10) Patent No.: US 12,322,481 B2
(45) Date of Patent: Jun. 3, 2025

(54) ANALYSIS OF SELECTIVELY NORMALIZED SPATIAL REPRESENTATIONS OF DATA

(71) Applicant: Multiplai Health Ltd., Cambridge (GB)

(72) Inventors: Santiago Gabriel Miriuka, Buenos Aires (AR); Mark Paul Ramondt, Buenos Aires (AR)

( * ) Notice: Subject to any disclaimer, the term of this patent is extended or adjusted under 35 U.S.C. 154(b) by 78 days.

(21) Appl. No.: 17/782,344

(22) PCT Filed: Dec. 4, 2020

(86) PCT No.: PCT/IB2020/061534
§ 371 (c)(1),
(2) Date: Jun. 3, 2022

(87) PCT Pub. No.: WO2021/111410
PCT Pub. Date: Jun. 10, 2021

(65) Prior Publication Data
US 2023/0005576 A1    Jan. 5, 2023

Related U.S. Application Data

(60) Provisional application No. 62/944,063, filed on Dec. 5, 2019.

(51) Int. Cl.
*G06T 7/00* (2017.01)
*G16H 10/60* (2018.01)

(52) U.S. Cl.
CPC .......... *G16H 10/60* (2018.01); *G06T 7/0012* (2013.01)

(58) Field of Classification Search
CPC .................................................. G06T 7/0012
See application file for complete search history.

(56) References Cited

U.S. PATENT DOCUMENTS

| | | | | |
|---|---|---|---|---|
| 2013/0089248 A1* | 4/2013 | Remiszewski | ....... | G06V 20/698 382/128 |
| 2014/0220580 A1* | 8/2014 | Brown | ............... | G01N 33/6893 435/6.12 |

FOREIGN PATENT DOCUMENTS

WO    2019200410 A1    10/2019

OTHER PUBLICATIONS

Henry Han published "A high performance profile-biomarker diagnosis for mass spectral profiles" in 22nd International Conference on Genome Informatics Busan, Korea in Dec. 2011, 16 pages.

(Continued)

*Primary Examiner* — Ayodeji O Ayotunde
(74) *Attorney, Agent, or Firm* — RC Trademark Company

(57) ABSTRACT

A computer that analyzes data is described. During operation, the computer may access the data in the memory. Then, the computer may transform the data into a spatial representation. For example, for biological data, the transformation may be based at least in part on a predefined relationship between the biological data and corresponding spatial locations in a genome. Moreover, the computer may selectively normalize the transformed data to obtain normalized transformed data. Notably, the selective normalization may use different normalization ranges based at least in part on expression levels in a type of biological sequencing. Next, the processor may convert the normalized transformed data into an output image. Furthermore, the processor may analyze the image using an image-analysis technique (such as a pretrained neural network) to determine a classification. Additionally, the processor may perform: storing the classification; displaying the classification; and/or providing the classification to an electronic device.

20 Claims, 8 Drawing Sheets

(56) References Cited

OTHER PUBLICATIONS

Jennifer et al. published "Selective normalisation of regional brain bis(monoacylglycero)phosphate in the mucopolysaccharidosis 1 (Hurler) mouse" in Experimental Neurology 277 (2016) 68-75 in Dec. 2011, 16 page.
International Search Report and Written Opinion of the International Searching Authority issued in International Patent Application No. PCT/IB2020/061534 on Mar. 5, 2021, 15 pages.

\* cited by examiner

ANALYSIS OF SELECTIVELY NORMALIZED SPATIAL REPRESENTATIONS OF DATA

CROSS-REFERENCE TO RELATED APPLICATIONS

The application claims the priority benefit of U.S. Provisional Patent Application Ser. No. 62/944,063, filed Dec. 5, 2019, the contents of which are herein incorporated by reference in their entirety.

BACKGROUND

Field

The described embodiments relate, generally, to techniques for analyzing data by transforming the data into a selectively normalized, two-dimensional (2D) spatial representation.

Related Art

Recent advances in the sequencing of biological samples has resulted in ever-larger datasets. For example, biological samples can be sequenced to determine genomic, transcriptomic, epigenomic, proteomic, and/or metabolic information. In principle, these large datasets can be analyzed to increase understanding of underlying biologic processes, to identify the pathophysiology of disease, to diagnose medical conditions, and to guide patient care.

However, in practice it is typically difficult to analyze biological datasets. Notably, the large size of biological datasets is often a computational challenge. Moreover, gaps in existing knowledge usually complicate or obstruct the analysis.

SUMMARY

A computer that analyzes data is described. This computer includes: an interface circuit, a processor, and memory that stores the data. During operation, the processor may access the data in the memory. Then, the processor may transform the data into a spatial representation. Moreover, the processor may selectively normalize the transformed data to obtain normalized transformed data. Next, the processor may convert the normalized transformed data into an output image. Furthermore, the processor may analyze the image using an image-analysis technique to determine a classification. Additionally, the processor may perform at least one of: storing the classification in the memory; displaying the classification on a display; or providing, from the interface circuit, the classification addressed to an electronic device.

Note that the data may include temporal data (such as longitudinal data).

Moreover, the data may include spatial data.

Furthermore, the data may include biological data, and the transformation may be based at least in part on a predefined relationship between the biological data and corresponding spatial locations in a genome. For example, the biological data may include: genomic data, proteomics data, transcriptomic data, epigenomic data, mitochondria data, electrical signals, and/or metabolic data.

Additionally, a given pixel in the image may represent a predefined or predetermined range of bases in the genome. Moreover, the image may have a dynamic or a variable encoding, so that at least some pixels represent different ranges of bases in the genome. For example, the variable encoding may be based at least in part on different information content in different portions of the data (such as mutual information or entropy). Alternatively, the image may have a fixed encoding, so that the given pixel represents a constant range of bases in the genome.

In some embodiments, the image-analysis technique includes a pretrained neural network.

Note that a given pixel in the image may represent data from multiple biological samples.

Moreover, different pixels in the image may correspond to different types of tissue or different types of biological samples.

Furthermore, the selective normalization may involve: using a first normalization range for data having a first intensity less than a threshold; and using a second (different) normalization range for data having a second intensity greater than the threshold. Note that a given intensity may correspond to an expression level in a type of biological sequencing.

In some embodiments, a given pixel in the image has an associated intensity and a color in a color space (such as RGB or YCbCr).

In some embodiments, a method of diagnosing a condition is also performed by a computer. The method may include any one or more of the preceding steps or features.

Another embodiment provides a computer-readable storage medium for use with the computer. This computer-readable storage medium includes program instructions for at least some of the operations performed by the computer.

Another embodiment provides a method for analyzing data. This method includes at least some of the operations performed by the computer.

Another embodiment provides an integrated circuit that performs at least some of the operations performed by the computer.

This Summary is provided merely for purposes of illustrating some exemplary embodiments, so as to provide a basic understanding of some aspects of the subject matter described herein. Accordingly, it will be appreciated that the above-described features are merely examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE FIGURES

Note that like reference numerals refer to corresponding parts throughout the drawings. Moreover, multiple instances of the same part are designated by a common prefix separated from an instance number by a dash.

DETAILED DESCRIPTION

Figure 1:
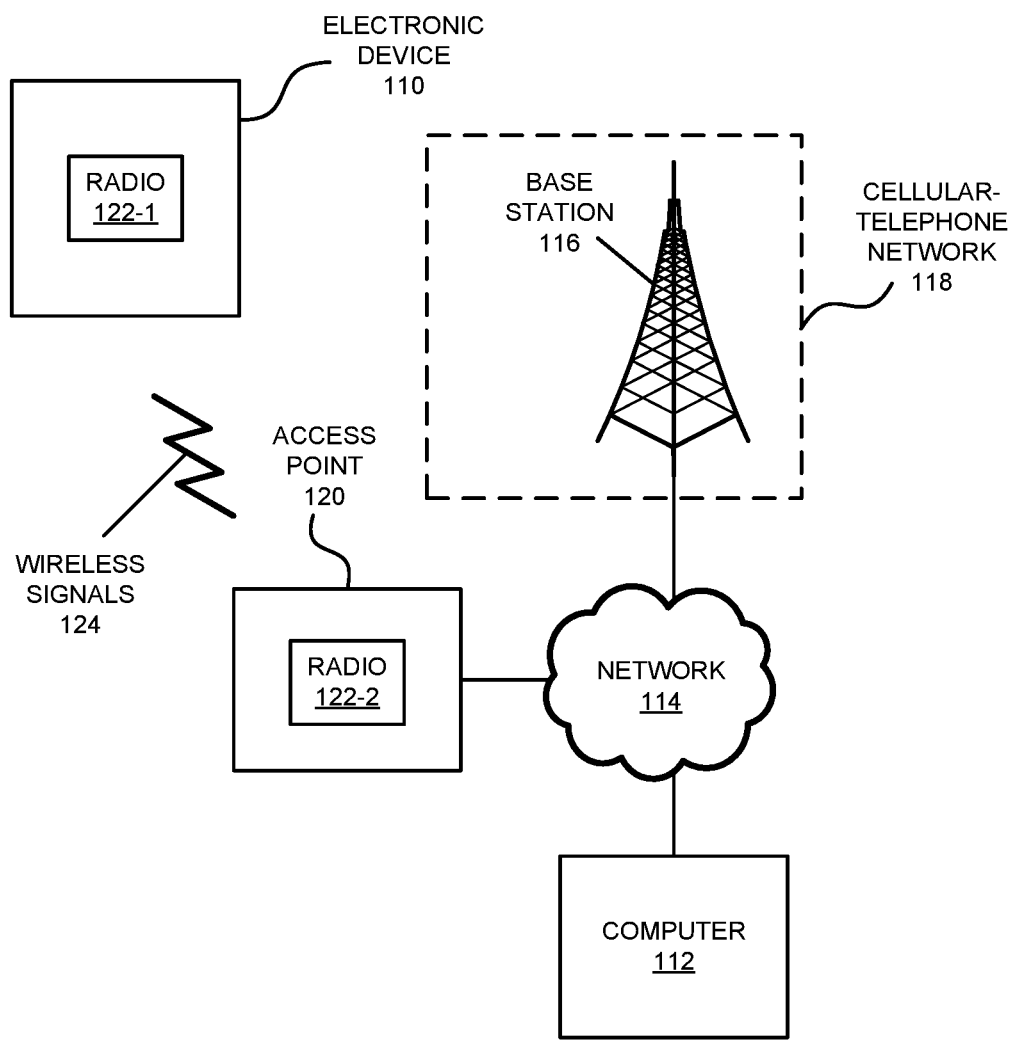
FIG. 1 is a block diagram illustrating an example of communication among electronic devices in accordance with an embodiment of the present disclosure.

A computer that analyzes data is described. During operation, the computer may access the data in the memory. Then, the computer may transform the data into a spatial representation. For example, the data may include biological data, and the transformation may be based at least in part on a predefined relationship between the biological data and corresponding spatial locations in a genome. Moreover, the computer may selectively normalize the transformed data to obtain normalized transformed data. Notably, the selective normalization may use different normalization ranges based at least in part on expression levels in a type of biological sequencing. Next, the processor may convert the normalized transformed data into an output image. Furthermore, the processor may analyze the image using an image-analysis technique (e.g., deep learning, pretrained or not pretrained neural network) to determine a classification. Additionally, the processor may perform: storing the classification in memory; displaying the classification on a display; and/or providing the classification to an electronic device.

By analyzing the data, the analysis techniques may facilitate faster, cheaper and more-accurate classification. For example, by transforming the data into the image, the analysis techniques may leverage one or more image-analysis techniques to perform the classification. This capability may simplify the computations involved in analyzing the data. Consequently, the analysis techniques may improve the user experience when analyzing data.

In the discussion that follows electronic devices and computers may include radios or, more generally, network interfaces that communicate packets or frames in accordance with one or more communication protocols, such as: an Institute of Electrical and Electronics Engineers (IEEE) 802.11 standard (which is sometimes referred to as 'Wi-Fi®,' from the Wi-Fi® Alliance of Austin, Texas), Bluetooth™ (from the Bluetooth Special Interest Group of Kirkland, Washington), a cellular-telephone communication protocol, another type of wireless interface, a wired network communication protocol (e.g., Ethernet, Ethernet II or an IEEE 802.3 standard, which are individually or collectively henceforth referred to as 'Ethernet') and/or another network communication protocol. For example, the cellular-telephone communication protocol may include or may be compatible with: a $2^{nd}$ generation or mobile telecommunication technology, a $3^{rd}$ generation of mobile telecommunications technology (such as a communication protocol that complies with the International Mobile Telecommunications-2000 specifications by the International Telecommunication Union of Geneva, Switzerland), a $4^{th}$ generation of mobile telecommunications technology (such as a communication protocol that complies with the International Mobile Telecommunications Advanced specification by the International Telecommunication Union of Geneva, Switzerland), a $5^{th}$ generation of mobile telecommunications technology (International Mobile Telecommunications (IMT)-2020 network), and/or another cellular-telephone communication technique. In some embodiments, the communication protocol includes Long Term Evolution or LTE. However, a wide variety of communication protocols may be used. In addition, the communication may occur via a wide variety of frequency bands.

FIG. 1 presents a block diagram illustrating an example of communication between an electronic device 110 (such as a computer, a portable electronic device, a cellular telephone, a tablet computer, a smartwatch, a wearable device, etc.) and the computer 112 (such as a cloud-based computer or server). Electronic device 110 and computer may communicate with each other using wired (or non-wireless communication) via network 114 (such as the Internet) and/or optional wireless communication via a cellular-telephone network 118 (e.g., via an optional base station 116), a wireless local area network (e.g., via an optional access point 120) and/or another wireless communication technique. Note that computer 112 may be located remotely from electronic device 110 (such as at a different geographic location) or in proximity to electronic device 110. Moreover, note that the optional access point 120 may provide access to network 114, such as the Internet, via an Ethernet protocol, and may be a physical access point or a virtual or 'software' access point that is implemented on a computer or an electronic device.

As described further below with reference to FIGS. 2-6, computer 112 may transform data into a spatial representation (such as a vector). Then, an image may be determined by selectively normalizing the transformed data. For example, the selective normalization may involve: using a first normalization range for data having a first read count less than a threshold, the first read count being transformed into a first intensity; and using a second (different) normalization range for data having a second read count greater than the threshold, the second read count being transformed into a second intensity. Note that a given intensity may correspond to an expression level in a type of biological sequencing. In some embodiments, a given pixel in the image may have an associated intensity and a color in a color space (such as RGB or YCbCr).

Moreover, computer 112 may perform an image-analysis technique on the image in order to classify the data. More generally, the image-analysis technique may be performed by one or more computers or electronic devices. In some embodiments, the image-analysis uses a pretrained neural network.

Additionally, computer 112 may perform at least one of: storing the classification in the memory; displaying the classification on a display; or providing the classification to electronic device 110.

Note that the data may include temporal data (such as longitudinal data) and/or spatial data. Furthermore, the data may include biological data, and the transformation may be based at least in part on a predefined relationship between the biological data and corresponding spatial locations in a genome. For example, the biological data may include: genomic data, transcriptomics data, proteomics data, epigenomic data, mitochondria data, microbiome data, electrical signals and/or metabolic data. In some embodiments, a given pixel in the image may represent data from multiple biological samples. Alternatively, or additionally, different pixels in the image may correspond to different types of tissue or different types of biological samples.

In these ways, the analysis techniques may be used to improve analysis of the data. Notably, the analysis techniques may allow one or more image-analysis techniques to be used to perform the classification. This capability may simplify the computations involved in analyzing the data, may reduce a cost of the analysis, may decrease a run time of the analysis, and/or may improve an accuracy of the classification. These capabilities may enhance the user experience of an individual or a user when using computer 112.

As noted previously, in some embodiments, communication among components in FIG. 1 involves wired and/or wireless communication. During the wireless communication, electronic device 110, the optional base station 116 and/or the optional access point 120 may: transmit advertising frames on wireless channels, detect one another by scanning wireless channels, establish wireless connections (for example, by transmitting association requests), and/or transmit and receive packets or frames (which may include the association requests and/or additional information as payloads). Moreover, during the wired communication, electronic device 110 and/or the computer 112 may receive packets or frames using a wired communication technique or protocol (e.g., Ethernet II or an IEEE 802.3 standard). In some embodiments, the optional base station 116 and/or the optional access point 120 may convert packets or frames that are received using the wired communication technique to a WLAN communication technique or protocol (such as an IEEE 802.11 standard or an LTE standard), and may wirelessly transmit the packets or frames. Similarly, the optional base station 116 and/or the optional access point 120 may: receive packets or frames using a wireless communication technique; convert the packets or frames to the wired communication technique; and transmit the packets or frames. Thus, the optional base station 116 and/or the optional access point 120 may perform the functions of an access point.

As described further below with reference to FIG. 7, electronic device 110, computer 112, the optional base station 116 and/or the optional access point 120 may include subsystems, such as: a networking subsystem, a memory subsystem and a processor subsystem. In addition, electronic devices 110, computer 112, the optional base station 116 and/or the optional access point 120 may include radios 122 in the networking subsystems. (Note that radios 122 may be instances of the same radio or may be different from each other.) More generally, electronic devices 110, computer 112, the optional base station 116 and/or the optional access point 120 can include (or can be included within) any electronic devices with the networking subsystems that enable electronic devices 110, computer 112, the optional base station 116 and/or the optional access point 120 to communicate with each other using wired communication (e.g., a non-wireless communication technique) and/or wireless communication. The wireless communication can comprise transmitting advertisements on wireless channels to enable electronic devices to make initial contact or detect each other, followed by exchanging subsequent data/management frames (such as association requests and responses) to establish a wireless connection, configure security options (e.g., Internet Protocol Security), and transmit and receive packets or frames via the wireless connection, etc.

As can be seen in FIG. 1, wireless signals 124 (represented by a jagged line) are optionally transmitted from radio 122-1 in electronic device 110. These wireless signals are optionally received by at least the optional access point 120. Notably, electronic device 110 may optionally transmit packets. In turn, these packets may be optionally received by a radio 122-2 in the optional access point 120. This may allow electronic device 110 to wirelessly communicate information to the optional access point 120. While FIG. 1 illustrates electronic device 110 transmitting packets, note that electronic device 110 may also receive packets from the optional access point 120.

In the described embodiments, processing of a packet or frame in electronic device 110, the optional base station 116 and/or the optional access point 120 includes: receiving signals (such as wireless signals 124) with the packet or frame; decoding/extracting the packet or frame from the received signals to acquire the packet or frame; and processing the packet or frame to determine information contained in the packet or frame.

Note that the communication among electronic device 110, computer 112, the optional base station 116 and/or the optional access point 120 may be characterized by a variety of performance metrics, such as: a data rate, a data rate for successful communication (which is sometimes referred to as a 'throughput'), an error rate (such as a retry or resend rate), a mean-square error of equalized signals relative to an equalization target, intersymbol interference, multipath interference, a signal-to-noise ratio, a width of an eye pattern, a ratio of number of bytes successfully communicated during a time interval (such as 1-10 s) to an estimated maximum number of bytes that can be communicated in the time interval (the latter of which is sometimes referred to as the 'capacity' of a channel or link), and/or a ratio of an actual data rate to an estimated data rate (which is sometimes referred to as 'utilization').

Although we describe the network environment shown in FIG. 1 as an example, in alternative embodiments, different numbers or types of electronic devices may be present. For example, some embodiments comprise more or fewer electronic devices. As another example, in another embodiment, different electronic devices are transmitting and/or receiving packets or frames. While electronic device 110 and optional access point 120 are illustrated with a single instance of radios 122, in other embodiments electronic device 110, optional access point 120 and/or another component in FIG. 1 may include multiple radios.

Figure 2:
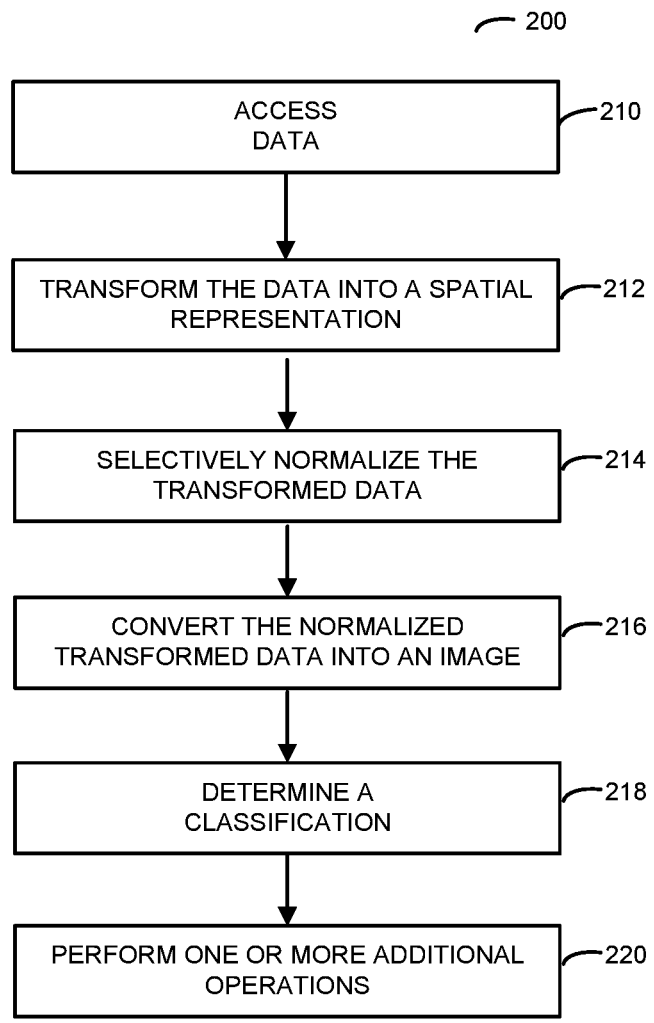
FIG. 2 is a flow diagram illustrating an example method for analyzing data in accordance with an embodiment of the present disclosure.

We now describe embodiments of the analysis techniques. FIG. 2 presents a flow diagram illustrating example method 200 for analyzing data, which may be performed by a computer, such as computer 112 in FIG. 1. During operation, the computer may access data (operation 210) in memory. For example, the data may include temporal data (such as longitudinal data) and/or spatial data. For example, continuous time data may be segmented into temporal subsets based at least in part on a delimiter, such as fixed events in a timeline. Moreover, the data may include biological data, and the transformation may be based at least in part on a predefined relationship between the biological data and corresponding spatial locations in a genome. In some embodiments, the biological data includes: genomic data, proteomics data, transcriptomic data, epigenomic data, mitochondria data, microbiome data, electrical signals, and/or metabolic data.

Then, the computer may transform the data into a spatial representation (operation 212). Moreover, the computer may selectively normalize the transformed data (operation 214) to obtain normalized transformed data. For example, the selective normalization may involve: using a first normalization range for data having a first read count less than a threshold (such as, e.g., a threshold of 10 or 100 in a range of 0 to 255); and using a second (different) normalization range for data having a second read count greater than the threshold. The first normalization range may be transformed into a first intensity range (e.g., 0 to 255 for RGB) and the second normalization range may be transformed in a second intensity range (e.g., 128 to 255 for RGB). Note that a given intensity may correspond to an expression level in a type of biological sequencing.

Next, the computer may convert the normalized transformed data into an output image (operation 216). In some embodiments, a given pixel in the image has an associated intensity and a color in a color space (such as RGB or YCbCr).

Note that a given pixel in the image may represent a predefined or predetermined range of bases in the genome. Moreover, the image may have a dynamic or a variable encoding, so that at least some pixels represent different ranges of bases in the genome. For example, the variable encoding may be based at least in part on different information content in different portions of the data (such as mutual information or entropy). Alternatively, the image may have a fixed encoding, so that the given pixel represents a constant range of bases in the genome. In some embodiments, a given pixel in the image may represent data from multiple biological samples, and/or different pixels in the image may correspond to different types of tissue or different types of biological samples.

Furthermore, the computer may analyze the image using an image-analysis technique to determine a classification (operation 218). For example, the image-analysis technique may include a pretrained neural network, an untrained neural network, or any other machine learning technique for data classification (i.e., supported vector machines).

Additionally, the computer may perform one or more additional operations (operation 220), including at least one of: storing the classification in the memory; displaying the classification on a display; or providing, from the interface circuit, the classification to an electronic device.

Note that method 200 may include additional or fewer operations. Moreover, there may be different operations. Furthermore, the order of the operations may be changed, and/or two or more operations may be combined into a single operation or performed at least partially in parallel.

While the preceding discussion illustrated the analysis techniques using a pretrained neural network, in other embodiments the analysis techniques may include or may use one or more pretrained machine-learning models. For example, during the analysis of the image (operation 218), the computer may perform one or more feature extraction techniques on the image to determine one or more features. For example, the one or more feature extraction techniques may include: a discrete Fourier transform, principal component analysis and/or JPEG (or compression) analysis. In some embodiments, the one or more feature extraction techniques includes one or more of: an edge or a line-segment detector (such as a Sobel-Feldman operator or Sobel Filter), a texture-based feature detector, a texture-less feature detector, a scale invariant feature transform (SIFT)-like object-detector, a speed-up robust-features (SURF) detector, a binary-descriptor (such as ORB) detector, a binary robust invariant scalable keypoints (BRISK) detector, a fast retinal keypoint (FREAK) detector, a binary robust independent elementary features (BRIEF) detector, a histogram of oriented gradients (HOG), a features from accelerated segment test (FAST) detector, a motion detector (such as a Gaussian-mixture model), etc. After the one or more features are determined, the computer may select a subset of the one or more features. The selected one or more features may be used as inputs to a pretrained machine-learning model that outputs the classification.

Note that the pretrained machine-learning model may be trained using a training dataset and, e.g., gradient descent optimization. For example, the computer may analyze the image using a pretrained classifier or a regression model that was trained using a supervised learning technique (such as a support vector machine, a classification and regression tree, logistic regression, LASSO, linear regression and/or another linear or nonlinear supervised-learning technique). In some embodiments, the one or more pretrained machine-learning models are trained using an unsupervised learning technique (such as a clustering technique).

Moreover, note that the image may be compatible with a wide variety of different resolutions and/or file formats, such as one or more of: a JPEG or JPEG File Interchange format, JPEG 2000, an Exchangeable image file format (Exif), a Tagged Image File Format (TIFF), a Graphics Interchange Format (GIF), a bitmap file format (such as BMP), a Portable Network Graphics (PNG) file format, a Netpbm format, a WebP format, a Better Portable Graphics (BPG) format, a Photoshop file format (from Adobe Systems of San Jose, California), a High Efficiency Image File Format (HEIF) and/or another image file format. Alternatively or additionally, in embodiments where the image includes a video (such as a sequences of images corresponding to a sequence of data), the video may be compatible with a variety of different resolutions and/or file formats, such as one or more of: an Audio Video Interleave (AVI) format, a Flash Video Format (FVF or SWF), a Windows Media Video (WMV), a Quick Time video format, Moving Pictures Expert Group 4 (MPEG 4 or MP4), an MOV format, a matroska (MKV) format, an advanced vide coding, high definition (AVCHD) format, and/or another video file format.

While FIG. 2 illustrated the computer performing the operations in method 200, in other embodiments two or more computers may perform some or all of the operations. For example, after generating the image (operation 216), the computer may provide the image to another computer (or computer system) that performs the analysis of operation 218.

Moreover, in some embodiments, the computer may automatically perform one or more measurements (e.g., using a sensor or a measurement device) that determine the data. For example, the computer may sequence a biological sample to determine the data.

Figure 3:
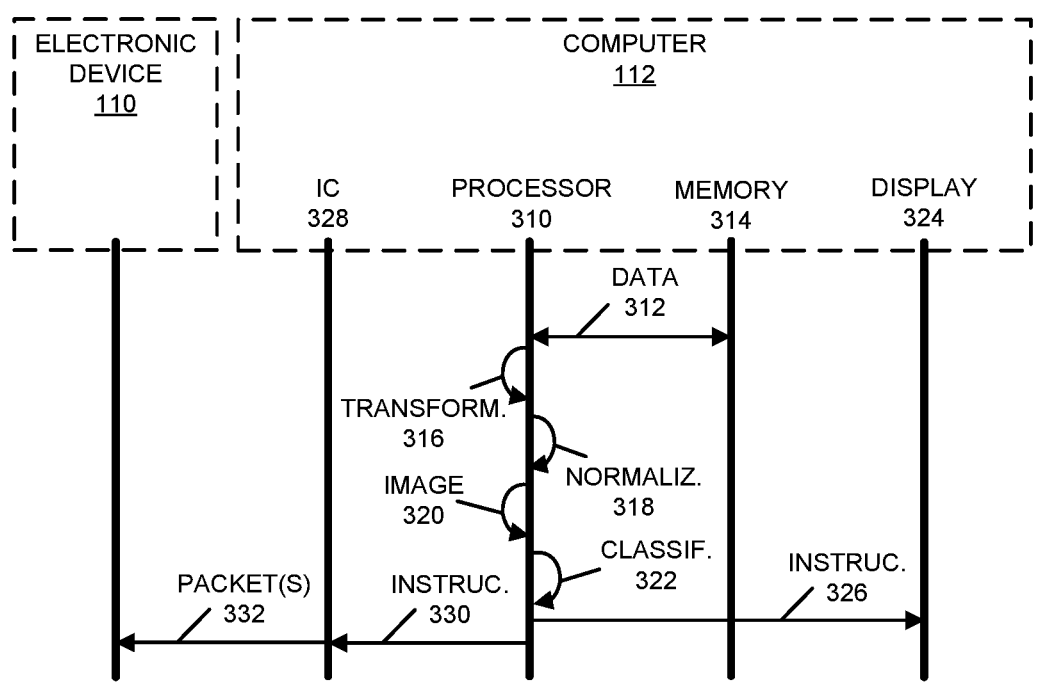
FIG. 3 is a drawing illustrating example communication among components in an electronic device in FIG. 1 in accordance with an embodiment of the present disclosure.

FIG. 3 presents a drawing illustrating example communication among components in computer 112 while performing method 200 (FIG. 2) and between computer 112 and electronic device 110. During operation, processor 310 in computer 112 may access data 312 in memory 314 in computer 112. Then, processor 310 may transform 316 data 312 into a spatial representation (SR). Moreover, processor 310 may selectively normalize 318 the transformed data to obtain normalized transformed data.

Next, processor 310 may convert the normalized transformed data into an output image 320. Furthermore, processor 310 may analyze image 320 using an image-analysis technique to determine a classification 322 (and, more generally, an analysis result).

Additionally, processor 310 may perform at least one of: storing classification 322 in memory 314; displaying classification 322 on a display 324 in computer 112 (such as by providing an instruction 326 to display 324 to display classification 322 or information corresponding to classification 322); or providing, from an interface circuit 328, classification 322 to electronic device 110 (such as by providing an instruction 330 to interface circuit 328 to provide one or more packets 332 or frames with classification 322 to electronic device 110).

While FIG. 3 illustrates particular operations involving unilateral or bilateral communication (as illustrated by single-arrow and dual-arrow lines), in general each of the operations illustrated in FIG. 3 may involve unilateral or bilateral communication.

In some embodiments, the analysis techniques are used to concurrently analyze the data. For example, the analysis techniques may use deep learning to: classify colormap images into different cancer classes; diagnose cancers; determine a colormap of transcripts in a biological sample; and/or expression at a point or locus of a genome of a biological lifeform (such as a human, an animal, a plant, an insect, etc.). In general, the analysis techniques may be used with a wide variety of data, such as: DNA, RNA, proteomic data, epigenomic data, etc.

During the analysis techniques, the spatial representation may align the data with a genome, may convert the transformed data into a colormap (e.g., an image), and then may analyze the image to determine the classification (with high accuracy, e.g., close to 100%). This analysis approach may significantly reduce a data file size from gigabytes to kilobytes. Note that each pixel in the image may represent N bases in the genome, where N is an integer. For example, each pixel may represent 10,000 bases in the genome. Alternatively, each pixel may represent a given chromosome, a single base, or another subset of information.

For example, the computer may receive or may access Fast-Seq raw data. After verifying the quality of the raw data, the computer may determine how to align the raw data to a genome. This calculation may involve the computer quantifying a number of transcripts/gene (e.g., there may be up to 200,000 different transcripts). Then, the computer may transform the data into an image, and align the transcripts with actual genomic positions in the image. Note that the output may indicate a level of expression at the actual position in genome in an image.

Using genomic data as an example, the computer may receive genes aligned to genome and transform them into an image in which each pixel equals a gene or N bases (where N is an integer) or a chromosome. In some embodiments, there may be 2 million pixels in an image.

The image may use an RGB color space and, more generally, may use a multi-level machine-readable code (e.g., similar to a QR code) to represent a relationship between transcripts and the genome. For example, the intensity of the RBG color may correspond to level of expression. An arbitrary color in the color space may be specified by combining red, green and/or blue colors. Notably, each red, green or blue color may be, e.g., represented by a number between 0 and 255, where '0' is turned off and '255' is maximum brightness. Consequently, each pixel may be represented by three numbers between 0 and 255. Thus, r:250, g:10 and b:240 (or 250, 10, 240) may specify purple, or r:100, g:100 and b:0 (or 100, 100, 10) may specify dark yellow. In some embodiments, a YCbCr color space may be used.

In an image, a given pixel may represent the same information across one or more biological samples. In addition, the given pixel may represent the same information in a training dataset for the image-analysis technique, such as a machine-learning model, a neural network, etc. Thus, a range of bases in chromosome 1 may represented by a pixel in an upper left-hand corner of an image, etc. Note that no expression may be represented by the color black. It may be possible that only 2% of a genome may be a color other than black, since only a minor part of the gene expression is detected, based, at least in part, on the depth of sequencing.

In some embodiments, a given pixel, which corresponds to a genomic location and transcript expression, may also represent: a time and a transcript relationship, a position and a transcript relationship, a tissue location and a transcript relationship (e.g., based at least in part on the expression of tissue specific genes), etc.

Because an image may have one or more layers, for example three layers, e.g., red, green and blue, where each color has the same information but potentially the same or different orientations, an image may include redundant information. In principle, different colors may be used to represent different information (such as genome, transcriptome, and proteome). For example, a given color may represent a subset of the total genome (e.g., chromosome 1-7 may be represented by one color, chromosome 8-16 by another color, and chromosome 17-23 and mitochondria by a third color). Consequently, an image may include one or more layers (such as one layer or three layers). Even more, an image may be formed by any number of overlaid layers, each one representing different information (for example, one layer per chromosome) and each one on a different or same color space and/or range. For example, chromosome 1 may be a whole layer as described elsewhere herein, but also a subset of a color dimension, ranging from 0 to 56 in the red channel, then chromosome 2 from 57 to 128, and so on, resulting in pixel intensity differences.

The biological sample(s) may be obtained from a variety of sources (such as RNAseq, short read sequencing, long read sequencing, of a biopsy sample). For example, the layers in an image may represent a cell from a single-cell RNAseq. The biological sample may be processed by using different technologies. For example, in some embodiments the biological sample may be analyzed using short-read cDNA reading (e.g., using Illumina technology) or using direct-RNA long reading (e.g., using Oxford Nanopore technology). The processing of the biological sample may or may not include preprocessing modifications. For example, a ribosomal and/or globin RNA depletion techniques may or may not be applied. In some embodiments, the biological sample may be obtained from one or more of: blood, urine, tissue, etc. Moreover, the data may be geo-localized to a position, such as microbiome expression at a particular location in the gut, electrical signals (such as frequency or voltage data) for a particular gastrointestinal location, voltage data for particular portion of heart, etc. Furthermore, the data may correspond to one or more of: RNA (such as transcriptomics, single-cell RNAseq, small RNAseq, circular RNA, and/or linear RNA), DNA, proteomics, epigenomics, etc. However, more generally, the data may include one or more of: in-situ stained sections, MRI data, EEG data, other electrical signals, etc. Additionally, a multi-layer image may be used to represent one or more types of data, such as genomic data, metabolic data, MRI data, EEG data, etc.

In some embodiments, the analysis techniques may use a pretrained or not pretrained neural network that may be further trained on a particular dataset. For example, 80% of images may be used for training and another 20% may be used for testing. Note that images may need to be processed similarly during training and analysis, so that comparisons can be made or pattern analysis can occur. Because it can be difficult to train a machine-learning model with a large data file, training may be facilitated by transforming the initial data to smaller image file without losing information using the analysis techniques described herein.

In an exemplary embodiment of the analysis techniques, a pipeline may start with a raw RNAseq data file. This input data file may be, e.g., several gigabytes in size, depending on how deep sequencing was performed. The data file may undergo transcriptomic analysis. For example, a quality-control check may be performed using a quality-control program, such as FASTQC (from Babraham Institute, Cambridge, UK). The adaptor sequences of the output file may be trimmed off using trimmomatic (Bolger, et al. (2014). "Trimmomatic: A flexible trimmer for Illumina Sequence Data." *Bioinformatics*, Vol. 30: Issue 15: pp. 2114-20, the disclosure of which is herein incorporated by reference in its entirety).

Next, Spliced Transcripts Alignment to a Reference or Spliced Transcripts Alignment to a Reference (STAR) (© Alexander Dobin) may be used to align the data to the genome, and the reads may be counted using HTSeq (from the Genome Biology Unit at the European Molecular Biology Laboratory of Heidelberg, Germany) for linear RNA (coding and noncoding) and DCC (from the Dieterich Lab at the University Hospital Heidelberg of Heidelberg, Germany) for circular RNA.

dom), which may contain gene names and their chromosome positions) may be generated. Notably, when perform the transformation, matching genes in the HTSeq counts and genecode files may be identified. For each match, the genome position (chromosome, start and end bases) and gene expression level may be included in the spatial representation.

Note that a number of bins in the spatial representation may be determined from the genome length divided by the number of pixels of the image. Consequently, the number of bins P in the spatial representation may equal the number of bases in chromosomes divided by the number of pixels in a given image. For example, for an image with 1024×1024 pixels, then for 3,088,286,401 bases in a genome, each bin may represent 2,945 bases. Thus, the number of bins may indicate a portion of the genome. Moreover, each bin may represent the RNA expression level in a particular portion.

Table 1 provides program instructions in bash to generate the spatial representation.

TABLE 1

```
! / bin /bash
gtf=annotation. gtf
mkdir files ready
out=files_ready
mkdir normcoverage
out1=norm_coverage
gtf_temp=$ (cat $ gtf | 'awk BEGIN{FS-"\t"} {split ($9, a, ";" ($3~"gene")
print a[1] "\ t "a[3] "\ t "$1 "\ t "$4"\ t "$5"\ t "a[5] "\ t "$7} ' | \
sed 's / gene_id" "//' sed 's / gene_id "// ' sed 's / gene_biotype "/ / ' sed '
   s/gene name "// ' | \
sed 's /gene_biotype "// ' | sed 's /"//g ' | sed 's///g ' | awk -F"\ t" '{split ($1, a,print
a[1], $2,
$3, $4, $5}')
for i in raw_data / * .counts
do
base=$(basename $ i.counts)
awk -F"\ t" '{split ($1, a, "."); print a[1], $2}' $i> raw_data/ $base.counts_tmp
   && mv raw_data/$base.counts_tmp raw_data/$base. counts
echo "$gtf temp" | awk 'FNR==NR{a[$1]=$2; next} (if (a[$1]=="")
   {a[$1]=0};
print $1"\ t "$2"\ t "$3"\ t "$4"\ t "$5"\ t "a[$1] "\ t" (a[$1] / (($5-$4)/1000))}'
   $i - > $out/$base.txt
sum=$ (cat $out/$base.txt | awk -F "\ t" '{s+=$7} END {print s} ') # sum total
   counts per sample (for normalization)
awk -v var="$sum" '{print $1"\ t "$2"\ t "$3"\ t "$4"\ t "$5"\ t "$6"\ t" (($7
   /(var/1000000)))}' $out / $base.txt > $out/$base.norm.txt
rm $out/$base.txt
echo "cove rage with counts (field6=fila 5)/tpm(field 7=fila 6) on file
   $base.norm"
python test_3.py $out/$base.norm. txt $outl/$base.csv
done
```

Figure 4:
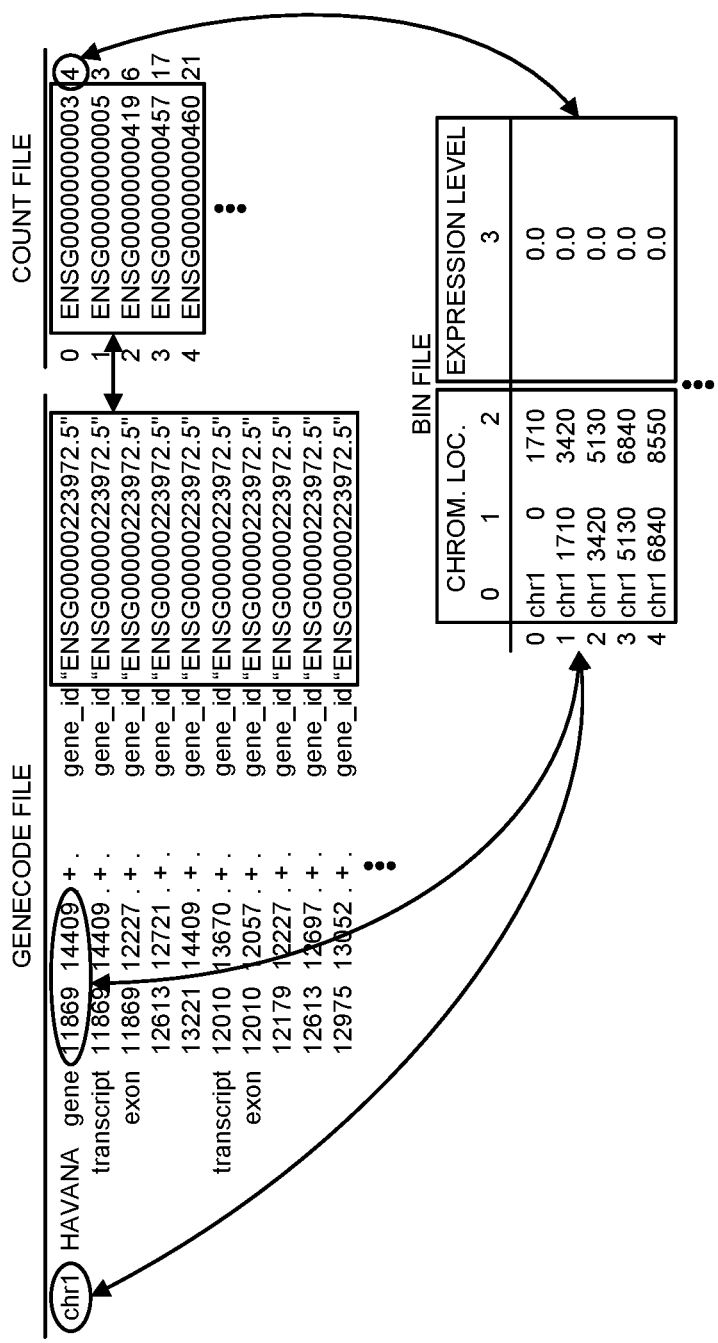
FIG. 4 is a drawing illustrating an example of transforming data into a spatial representation in accordance with an embodiment of the present disclosure.

Moreover, as shown in FIG. 4, which presents a drawing illustrating an example of transforming data into a spatial representation, the gene expression level data may be combined with or aligned with genome position. For example, a file combining the HTSeq-counts with genecode (from the Wellcome Trust Sanger Institute of Hinxton, United King- Table 1 (Continued).

Table 2 provides program instructions in python to use the output of the program instructions in Table 1 to generate the spatial representation by merging gtf and a gene expression file. These program instructions include the binning definition.

TABLE 2

```
import sys
chromos={ }
length =[248956422, 242193529, 198295559, 190214555, 181538259,
   170805979, 159345973, 145138636, 138394717, 133797422, 135086622,
   133275309, 114364328, 107043718, 101991189, 90338345, 83257441,
   80373285, 58617616, 64444167, 46709983, 50818468, 156040895,
   57227415, 16569]
bining=1710
def filecounter(filename, chromos):
```

TABLE 2-continued

```
    filepath = filename
    with open(filepath) as fp:
        for line in fp:
            row=line.split( )
            start=int (int (row[3]) / bining ) * bining
            chromos [row[2] ] [ str (start)]+=float (row[6])
            end=int (int (row [4]) / bining ) * bining
            for j in range (start+bining, end+bining, bining):
                chromos [row[2] ] [str(j)]+=float (row[6])
for i in range (1, 26):
    if i==23:
        chromo='X'
    elif i==24:
        chromo='Y'
    elif i==25:
        chromo='M'
    else:
        chromo=str(i)
    chromos.update({ 'chr'+chromo: { } })
    for j in range (0, largos [i -1], bining):
        chromos ['chr'+chromo].update ({str (j): 0})
filename_in=sy s. argv [1]
filename_out=sys. argv[2]
filecounter(fdename_in, chromos)
f = open(filename_out , 'a')
for i in range (1, 26):
    if i==23:
        chromo='X`
    elif i==24:
        chromo='Y`
    elif i==25:
        chromo='M`
    else :
        chromo=str(i)
    for j in range (0, length[i-l], bining):
        chromos['chr`+chromo] [str(j)]
        f.write(' \n ' + ' chr '+chromo +' , '+ str(j) +' , '+ str (j+bining) +' , '+
            str(chromos[' chr '+chromo] [str(j)]))
f.close()
```

Table 2 (Continued).

Moreover, the file with the name of each gene, position, and expression level may be normalized according to its expression level. Normalization may be performed based on a count number (e.g., level of expression, number of transcripts per million, number of reads, etc.) and transformed into a reference range of 0 to 256, which are values that corresponds to an RGB image. In some embodiments of the analysis techniques, a double normalization is performed according to the gene expression level. For example, genes with a gene expression level that is less than a threshold value may be normalized from, e.g., 0 to 256. Moreover, genes with a gene expression level that is greater than the threshold value may be normalized to a number between, e.g., 128 to 256. The double normalization may enhance the representation of low-expressed genes. Otherwise, many pixels in the image may be black.

Figure 5:
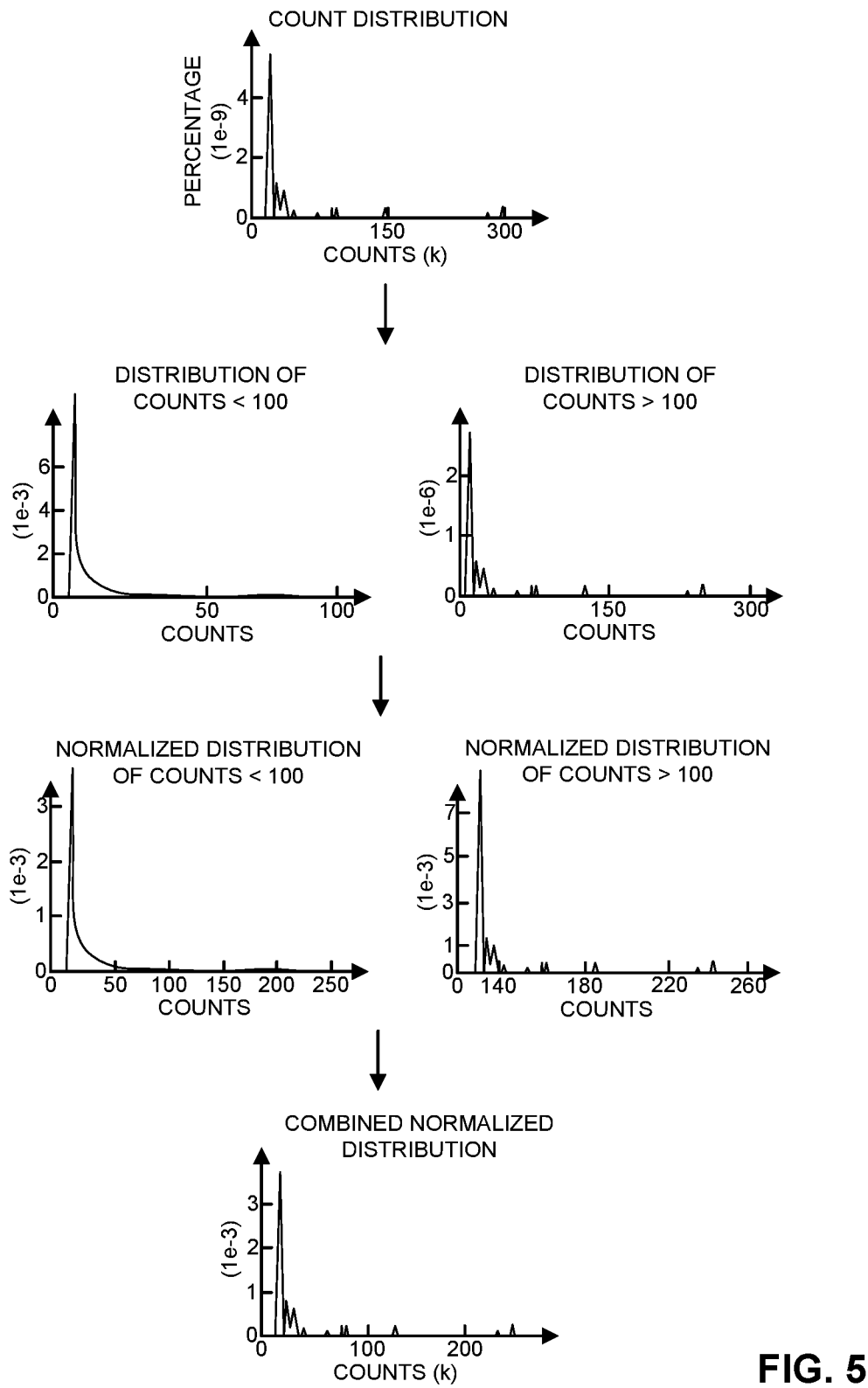
FIG. 5 is a drawing illustrating an example of selective normalization in accordance with an embodiment of the present disclosure.

This is illustrated in FIG. 5, which presents a drawing illustrating an example of selective normalization. Notably, in the initial transcriptomic distribution, most of the reads have a low number of counts. If this data is normalized to a range from 0 to 255, the resulting distribution may be skewed, with most genes having very low values. Consequently, the resulting image may be mostly black. In addition, genes with low expression are often long noncoding RNA, which may account for most differences between different types of tissue. Without the double normalization, highly expressed genes (such as coding RNA) may obscure the long noncoding RNA.

In order to avoid these problems, the data may be split between high and low-expressed genes. For example, 100 transcripts/million or 100 reads may be used as a split point between coding genes and noncoding genes. Alternatively, a split point or threshold value may be determined for a particular distribution. After splitting, the data may be separately normalized, such as from 0 to 255 for low expressed genes, and from 128 to 255 in highly expressed genes. Next, both normalizations may be joined in a single distribution.

Furthermore, after the double normalization, the transformed and normalized data may be converted into an image. Notably, the gene expression level may be normalized to an RGB image value. An RGB image may be formed by overlapping three different layers of numbers called channels. A first channel may be used for red, a second channel may be used for green and a third channel may be used for blue. The number of each layer may span from 0 (darkest) to 255 (lighter). Thus, a pixel with a value of (0,0,0) may be black, while a value of (255,255,255) may be white, and a pixel with a value of (255,0,0) may be pure red.

Figure 6:
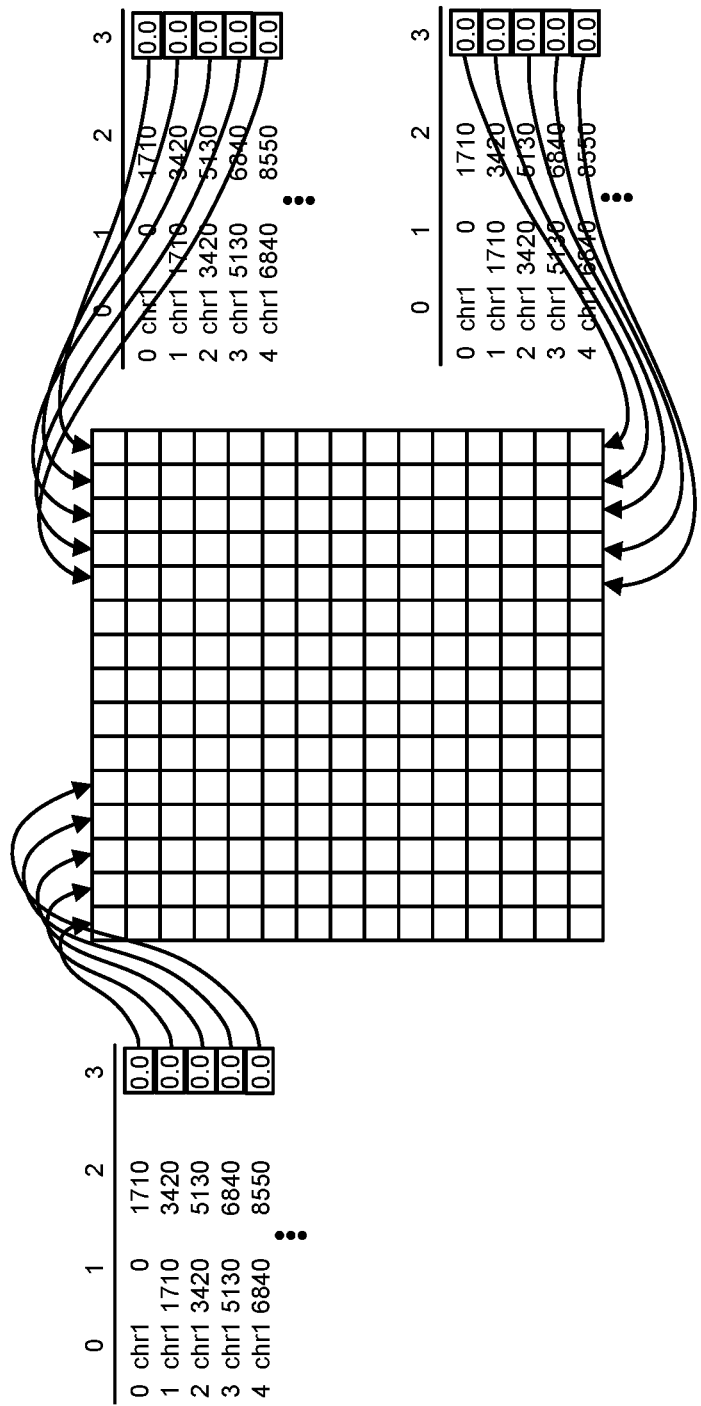
FIG. 6 is a drawing illustrating an example of converting transformed data into an image in accordance with an embodiment of the present disclosure.

This is illustrated in FIG. 6, which presents an example of converting transformed data into an image. Notably, a bin file may be translated into an image by converting each row into a pixel. For example, a first row may take a first position, and so on. Moreover, a red channel may start at the upper left corner, a green channel may start at the upper right, and a blue channel may start at a lower right. In some embodiments, after the bins in chromosome 1 have been placed, the process may continue with the next chromosome. Note that the bin file may include information for somatic, sexual, and mitochondrial chromosomes.

Table 3 provides program instructions in python to generate the image. Notably, the program instructions may generate a function that is applied to every .csv file that is created by the program instructions in Tables 1 and 2.

TABLE 3

```
import numpy as np
from PIL import Image, ImageFilter
import cv2 as cv
import pandas as pd
from scipy import stats
import os
from sklearn.preprocessing import MinMaxScaler
    def create_img (indir, outdir):
        for root, dirs, filenames in os.walk (indir):
            for fde in filenames:
                if file.endswith('.csv'):
                    path_file = os.path.join(root, file)
                    df = pd.read_csv(path_file, header=0, names=['Chr',' Start
                        ','End ','Counts'])
                    cutoff = 100
                    less_cutoff = df.loc[df ['Counts '] <= cutoff]
                    df.loc[ df ['Counts'] <= cutoff, 'norm'] = (less_cutoff['Counts']
                        /(less_cutoff['Counts'].max( )*1)) *255
                    high_cutoff = df.loc[df ['Counts'] > cutoff]
                    df.loc[ df ['Counts '] > cutoff, 'norm'] = (((high_cutoff['Counts'
                        ] - high_cutoff ['Counts']min() )/((high_cutoff['Counts']
                        .max() - high_cutoff ['Counts']min( ))*2) + 0.5))*255
                    df_array = df.drop'Chr ',' Start ','End', 'Counts'],
                        axis=1). values
                    df_zeros = np.zeros((311, 1))
                    df_plus = np.concatenate((df_array, df_zeros))
                    y = 1806337
                    subred = df_plus[0:y]
                    sub_green = df_plus [0:y]
                    sub blue = df_plus [0:y]
                    z = 1344
                    red = sub_red.reshape((z , z))
                    green = sub_green.reshape((z , z))
                    blue = sub_blue.reshape((z , z))
                    green = np.rot90(green, 2)
                    blue = np.fliplr(blue)
                    arr = np.zerosz , z , 3))
                    arr [:, :, 0] = red
                    arr [:, :, 1]=green
                    arr [:, :,2] = blue
                    img = Image.fromarray(arr.astype(int), 'RGB')
                    img.save(outdir+file+'.png')
```

Table 3 (Continued).

After an image is created, a deep-learning technique may be used to perform the classification. For example, a convolutional neural network such as a residual neural network (ResNet) or a densely connected neural network (DenseNet), may be used to classify images created from one or more transcriptomic datasets. In some embodiments, using cancer data from the Genome Data Commons (from the National Cancer Institute of Bethesda, Maryland), the analysis techniques may be able to classify transcriptomics with an accuracy of 97.1%. In general, the classification may detect a disease, a trait, a state, a prognosis, a response to treatment, and/or the recurrence of a disease.

We now describe embodiments of an electronic device, which may perform the analysis techniques. FIG. 7 presents a block diagram of an example of an electronic device 700, such as one of: one of electronic devices 110, computer 112, the optional base station 116 or the optional access point 120. This electronic device includes processing subsystem 710, memory subsystem 712, networking subsystem 714 and optional measurement subsystem 732. Processing subsystem 710 includes one or more devices configured to perform computational operations. For example, processing subsystem 710 can include one or more microprocessors, application-specific integrated circuits (ASICs), microcontrollers, programmable-logic devices, one or more GPUs, and/or one or more digital signal processors (DSPs). In some embodiments, processing subsystem 710 includes a mean for processing or performing computations.

Memory subsystem 712 includes one or more devices for storing data and/or instructions for processing subsystem 710, networking subsystem 714 and/or measurement subsystem 732. For example, memory subsystem 712 can include dynamic random access memory (DRAM), static random access memory (SRAM), a read-only memory (ROM), flash memory, and/or other types of memory. In some embodiments, instructions for processing subsystem 710 in memory subsystem 712 include: one or more program modules or sets of instructions (such as program instructions 722 or operating system 724), which may be executed by processing subsystem 710. For example, a ROM can store programs, utilities or processes to be executed in a non-volatile manner, and DRAM can provide volatile data storage, and may store instructions related to the operation of electronic device 700. Note that the one or more computer programs may constitute a computer-program mechanism, a computer-readable storage medium or software. Moreover, instructions in the various modules in memory subsystem 712 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 710. In some embodiments, the one or more computer programs are distributed over a network-coupled computer system so that the one or more computer programs are stored and executed in a distributed manner.

In addition, memory subsystem 712 can include mechanisms for controlling access to the memory. In some embodiments, memory subsystem 712 includes a memory hierarchy that comprises one or more caches coupled to a memory in electronic device 700. In some of these embodiments, one or more of the caches is located in processing subsystem 710.

In some embodiments, memory subsystem 712 is coupled to one or more high-capacity mass-storage devices (not shown). For example, memory subsystem 712 can be coupled to a magnetic or optical drive, a solid-state drive, or another type of mass-storage device. In these embodiments, memory subsystem 712 can be used by electronic device 700 as fast-access storage for often-used data, while the mass-storage device is used to store less frequently used data.

Figure 7:
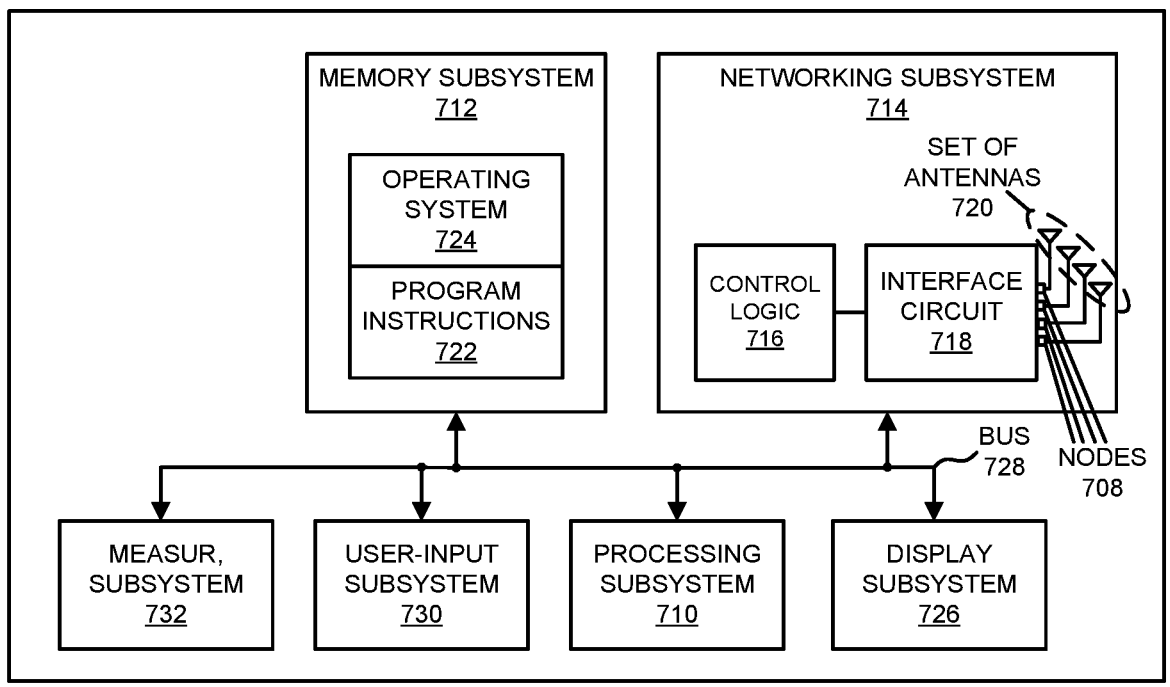
FIG. 7 is a block diagram illustrating an example of one of the electronic devices of FIG. 1 in accordance with an embodiment of the present disclosure.

Networking subsystem 714 includes one or more devices configured to couple to and communicate on a wired and/or wireless network (i.e., to perform network operations), including: control logic 716, an interface circuit 718 and a set of antennas 720 (or antenna elements) in an adaptive array that can be selectively turned on and/or off by control logic 716 to create a variety of optional antenna patterns or 'beam patterns.' (While FIG. 7 includes set of antennas 720, in some embodiments electronic device 700 includes one or more nodes, such as nodes 708, e.g., a pad, which can be coupled to set of antennas 720. Thus, electronic device 700 may or may not include set of antennas 720.) For example, networking subsystem 714 can include a Bluetooth networking system, a cellular networking system (e.g., a 3G/4G/5G network such as UMTS, LTE, etc.), a universal serial bus (USB) networking system, a networking system based on the standards described in IEEE 802.11 (e.g., a Wi-Fi® networking system), an Ethernet networking system, and/or another networking system.

Networking subsystem 714 includes processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for the network system. Moreover, in some embodiments a 'network' or a 'connection' between the electronic devices does not yet exist. Therefore, electronic device 700 may use the mechanisms in networking subsystem 714 for performing simple wireless communication between the electronic devices, e.g., transmitting advertising or beacon frames and/or scanning for advertising frames transmitted by other electronic devices.

Moreover, measurement subsystem 732 may include one or more sensors that can acquire one or more data (such as an image, an electrical signal, information corresponding to RNA or DNA, etc.). Furthermore, measurement subsystem 732 may optionally include one or more integrated circuits that perform at least some of the operations in an embodiment of the analysis techniques.

Within electronic device 700, processing subsystem 710, memory subsystem 712, networking subsystem 714 and measurement subsystem 732 are coupled together using bus 728 that facilitates data transfer between these components. Bus 728 may include an electrical, optical, and/or electro-optical connection that the subsystems can use to communicate commands and data among one another. Although only one bus 728 is shown for clarity, different embodiments can include a different number or configuration of electrical, optical, and/or electro-optical connections among the subsystems.

In some embodiments, electronic device 700 includes a display subsystem 726 for displaying information on a display, which may include a display driver and the display, such as a liquid-crystal display, a multi-touch touchscreen, a heads-up display, an augmented reality display, a virtual reality display, another type of display, etc. For example, the display be an HDMI display. Display subsystem 726 may be controlled by processing subsystem 710 to display information to a user. In some embodiments, display subsystem 726 is used to display processed or cleaned-up images following application of the analysis techniques.

Electronic device 700 can also include a user-input subsystem 730 that allows a user of the electronic device 700 to interact with electronic device 700. For example, user-input subsystem 730 can take a variety of forms, such as: a button, keypad, dial, touch screen, audio input interface, etc.

Electronic device 700 can be (or can be included in) any electronic device with at least one network interface. For example, electronic device 700 may include: a cellular telephone or a smartphone, a smartwatch, a wearable device (such as smart glasses or a helmet camera), a camera (such as a dashboard camera), a tablet computer, a laptop computer, a notebook computer, a personal or desktop computer, a netbook computer, a media player device, an electronic book device, a smartwatch, a wearable computing device, a portable computing device, a consumer-electronic device, a vehicle (such as a car, bus or truck), as well as any other type of electronic computing device having measurement and/or analysis capability.

Although specific components are used to describe electronic device 700, in alternative embodiments, different components and/or subsystems may be present in electronic device 700. For example, electronic device 700 may include one or more additional processing subsystems, memory subsystems, networking subsystems, imaging subsystems, measurement subsystems and/or display subsystems. Additionally, one or more of the subsystems may not be present in electronic device 700. Moreover, in some embodiments, electronic device 700 may include one or more additional subsystems that are not shown in FIG. 7. Also, although separate subsystems are shown in FIG. 7, in some embodiments some or all of a given subsystem or component can be integrated into one or more of the other subsystems or component(s) in electronic device 700. For example, in some embodiments program instructions 722 are included in operating system 724 and/or control logic 716 is included in interface circuit 718.

Moreover, the circuits and components in electronic device 700 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit (which is sometimes referred to as a 'communication circuit') may implement some or all of the functionality of networking subsystem 714. This integrated circuit may include hardware and/or software mechanisms that are used for transmitting wireless signals from electronic device 700 and receiving signals at electronic device 700 from other electronic devices. Aside from the mechanisms herein described, radios are generally known in the art and hence are not described in detail. In general, networking subsystem 714 and/or the integrated circuit can include any number of radios. Note that the radios in multiple-radio embodiments function in a similar way to the described single-radio embodiments.

In some embodiments, networking subsystem 714 and/or the integrated circuit include a configuration mechanism (such as one or more hardware and/or software mechanisms) that configures the radio(s) to transmit and/or receive on a given communication channel (e.g., a given carrier frequency). For example, in some embodiments, the configuration mechanism can be used to switch the radio from monitoring and/or transmitting on a given communication channel to monitoring and/or transmitting on a different communication channel. (Note that 'monitoring' as used herein comprises receiving signals from other electronic devices and possibly performing one or more processing operations on the received signals).

In some embodiments, an output of a process for designing an integrated circuit, or a portion of an integrated circuit, which includes one or more of the circuits described herein may be a computer-readable medium such as, for example, a magnetic tape or an optical or magnetic disk. The computer-readable medium may be encoded with data structures or other information describing circuitry that may be physically instantiated as the integrated circuit or the portion of the integrated circuit. Although various formats may be used for such encoding, these data structures are commonly written in: Caltech Intermediate Format (CIF), Calma GDS II Stream Format (GDSII) or Electronic Design Interchange Format (EDIF). Those of skill in the art of integrated circuit design can develop such data structures from schematic diagrams of the type detailed above and the corresponding descriptions and encode the data structures on the computer-readable medium. Those of skill in the art of integrated circuit fabrication can use such encoded data to fabricate integrated circuits that include one or more of the circuits described herein.

While some of the operations in the preceding embodiments of the analysis techniques were implemented in hardware or software, in general the operations in the preceding embodiments of the analysis techniques can be implemented in a wide variety of configurations and architectures. Therefore, some or all of the operations in the preceding embodiments of the analysis techniques may be performed in hardware, in software or both. For example, at least some of the operations in the analysis techniques may be implemented using program instructions 722, operating system 724 (such as a driver for interface circuit 718) or in firmware in measurement subsystem 732 or interface circuit 718. Alternatively or additionally, at least some of the operations in the communication technique may be implemented in a physical layer, such as hardware in interface circuit 718.

While the preceding embodiments are applicable to many biological samples (for example, blood, urine, tissue biopsies, etc.) from many different sources, an implementation may be the analysis of a blood sample. In such an embodiment, the sample is obtained by standard venipuncture in a peripheral vein and stored in a stabilization buffer (e.g., RNA-later) for long periods of time (e.g., days, months or years), for later analysis. The sample can be processed and analyzed on site or alternatively shipped to a central facility. The sample may be then processed to isolate RNA using any standard routine procedures (e.g., organic extraction methods, a spin basket format method, magnetic particles, direct lysis methods, etc.). Then the sample may be further processed to build up a cDNA library for RNA-sequencing. This step may or may not include any RNA specific separation technique, including Ribosomal or Globin RNA depletion. A cDNA library may be then built using reverse transcription from the RNA, and then a fragmentation and sequencer adapters may or may be not applied for obtaining a final sample. Then the sample can be sequenced for different number of reads (e.g., 40 million reads). According to the library preparation method of choice, either a short read RNA sequencing (for example, the Illumina technology) or a long-read RNA sequencing technique (using for example the Oxford Nanopore technology) may be applied.

Figure 8:
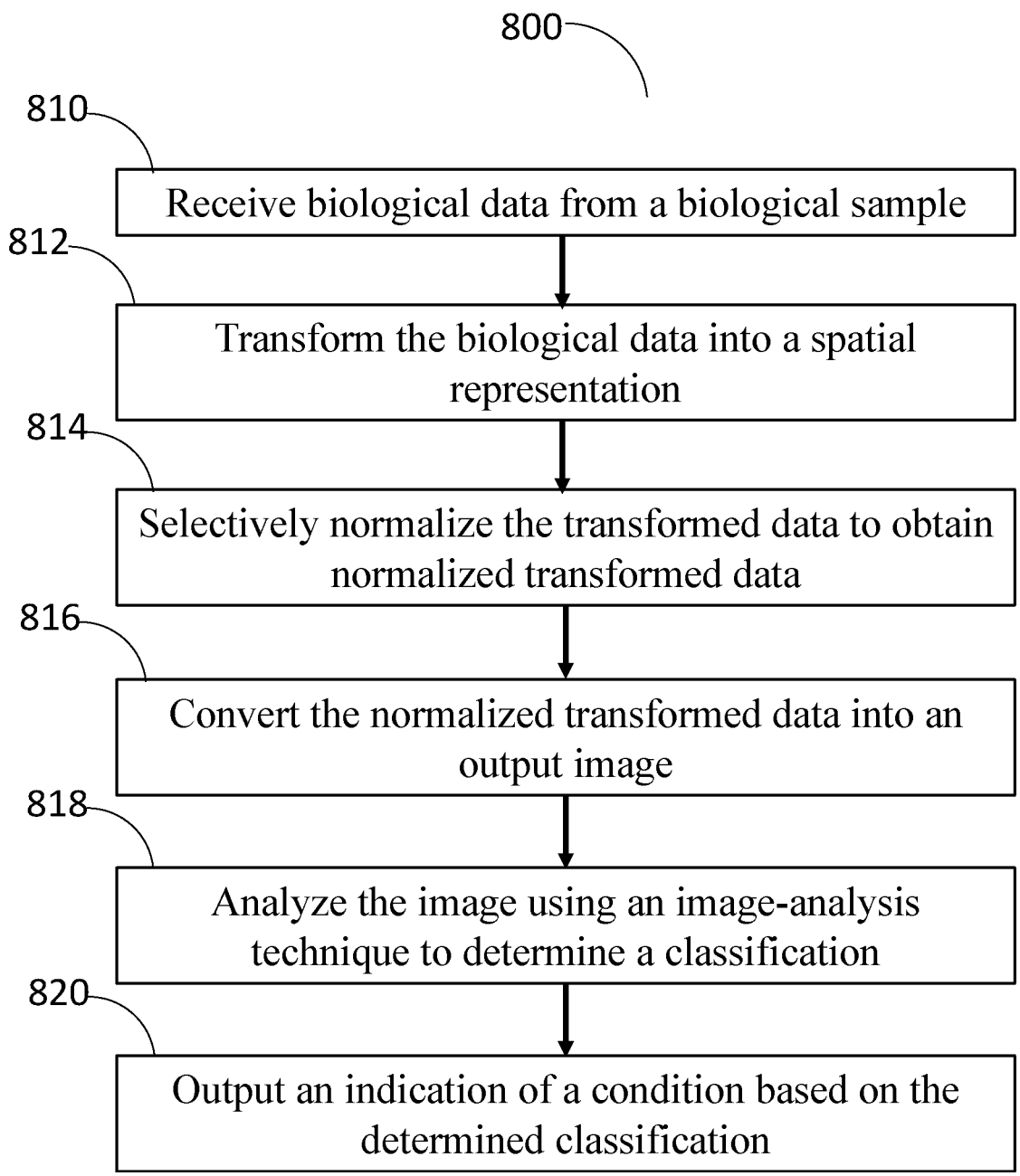
FIG. 8 is a flow diagram illustrating an example method of diagnosing a condition in accordance with an embodiment of the present disclosure.

Using any of the preceding embodiments or methods, a method of diagnosing, prognosing, monitoring, guiding treatment of, assessing, etc. a condition, disease, health state, etc. may be performed, as shown in FIG. 8. Method 800 may be performed by a computer, such as computer 112 in FIG. 1. During operation, the computer may receive biological data from a biological sample (operation 810). As described elsewhere herein, biological data may include, but not be limited to: genomic data, proteomics data, transcriptomic data, epigenomic data, mitochondria data, electrical signals, and/or metabolic data. The biological sample may include, but not be limited to, blood, saliva, tissue, stool, cerebral spinal fluid (CSF), urine, or any other type of tissue or fluid from a living being (e.g., animal, human, vertebrate, invertebrate, fish, reptile, bird, etc.). In some embodiments, the method 800 may optionally include receiving the biological sample, for example via collection, postal carrier, medical procedure, biopsy, swab, voiding, etc. In some embodiments, the method 800 may optionally include isolating the biological data from the biological sample. Isolation may include, but not be limited to, any one or more of: cell isolation; cell lysis; DNA isolation; protein isolation; RNA isolation; size-based exclusion or isolation; species based exclusion or isolation of DNA, RNA, and/or protein; genetic material amplification; genetic material synthesis; etc. In some embodiments, the computer, or another computer communicatively coupled to the computer, may optionally sequence the biological data from the biological sample, for example using long reads, short reads, complementary DNA (cDNA) methods, tunneling currents, antibody-based sequencing, etc.

In some embodiments, the computer may transform the biological data into a spatial representation (operation 812); selectively normalize the transformed data to obtain normalized transformed data (operation 814); convert the normalized transformed data into an output image (operation 816); and analyze the image using an image-analysis technique to determine a classification (operation 818), each of which have been described elsewhere herein, for example in FIG. 2.

In some embodiments, the computer may output an indication of a condition based on the determined classification (operation 820). Outputting an indication may include displaying a message, alert, pop-up, badge, or other notification on a display of a computing device, for example a mobile computing device, personal digital assistant, desktop computer, server, laptop, wearable, etc. The indication may include an audio (e.g., beeping, chime, spoken language, etc.), visual (e.g., light, text-based notification, color activation or change, etc.), or haptic indication (e.g., vibration, piezo based haptics, etc.).

In some embodiments, the condition, disease, health state, etc. includes, but is not limited to, a diagnosis, a disease state, a genetic status, a prognosis, etc. For example, a disease state may include an indication of abnormal versus normal, healthy versus not healthy, benign versus malignant, etc. Further for example, a genetic status may include, but not be limited to, one or more genetic markers, a mutation presence or absence, a gene presence or absence, a transposon presence or absence, a long non-coding RNA presence or absence, etc., any of which may or may not be indicative of a condition or disease. Further still, for example, a prognosis may include, but not be limited to, a life expectancy, a disease course, a likelihood of treatment success or failure, an expected or anticipated pain level, a likelihood of metastasis, a likelihood of acquiring or being diagnosed with a condition or disease or cancer, etc.

While examples of numerical values are provided in the preceding discussion, in other embodiments different numerical values are used. Consequently, the numerical values provided are not intended to be limiting.

In the preceding description, we refer to 'some embodiments.' Note that 'some embodiments' describes a subset of all of the possible embodiments but does not always specify the same subset of embodiments.

The foregoing description is intended to enable any person skilled in the art to make and use the disclosure and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown but is to be accorded the widest scope consistent with the principles and features disclosed herein.

What is claimed is:

1. A computer, comprising:
   an interface circuit configured to communicate with an electronic device;
   a processor; and
   memory configured to store biological data and program instructions, wherein, when executed by the processor, the program instructions cause the computer to analyze the biological data by performing operations comprising:
      accessing the biological data in the memory;
      transforming the biological data into a spatial representation, wherein the transformation is based at least in part on a predefined relationship between the biological data and corresponding spatial locations in a genome;
      selectively normalizing the transformed biological data to obtain normalized transformed data, wherein the selective normalization comprises using a first normalization range for data having a first read count less than a threshold, the first read count being transformed into a first intensity, and using a second normalization range for data having a second read count greater than the threshold, the second read count being transformed into a second intensity;
      converting the normalized transformed biological data into an output image, wherein a given pixel in the output image represents a predefined or predetermined range of bases in the genome;
      analyzing the image using an image-analysis technique to determine a classification to detect a disease, a trait, a state, a prognosis, a response to treatment, and/or the recurrence of a disease; and
      providing, from the interface circuit, the classification addressed to an electronic device.

2. The computer of claim 1, wherein the biological data comprises:
   temporal data or spatial data.

3. The computer of claim 1, wherein the image has a dynamic or a variable encoding, so that at least some pixels represent different ranges of bases in the genome.

4. The computer of claim 3, wherein the variable encoding is based at least in part on different information content in different portions of the biological data.

5. The computer of claim 1, wherein the image-analysis technique comprises a neural network.

6. The computer of claim 1, wherein a given pixel in the image represents data from multiple biological samples.

7. The computer of claim 1, wherein different pixels in the image correspond to different types of tissue or different types of biological samples.

8. The computer of claim 1, wherein a given intensity corresponds to an expression level in a type of biological sequencing.

9. A non-transitory computer-readable storage medium for use in conjunction with a computer, the computer-readable storage medium storing program instructions that, when executed by the computer, cause the computer to carry out operations to analyze biological data by performing operations comprising:
   accessing the biological data in memory;
   transforming the biological data into a spatial representation, wherein the transformation is based at least in part on a predefined relationship between the biological data and corresponding spatial locations in a genome;
   selectively normalizing the transformed data to obtain normalized transformed data, wherein the selective normalization comprises using a first normalization range for data having a first read count less than a threshold, the first read count being transformed into a first intensity, and using a second normalization range for data having a second read count greater than the threshold, the second read count being transformed into a second intensity;
   converting the normalized transformed data into an output image, wherein a given pixel in the output image represents a predefined or predetermined range of bases in the genome;
   analyzing the image using an image-analysis technique to determine a classification to detect a disease, a trait, a state, a prognosis, a response to treatment, and/or the recurrence of a disease; and
   providing, from the interface circuit, the classification addressed to an electronic device.

10. The non-transitory computer-readable storage medium of claim 9, wherein the biological data comprises: temporal data or spatial data.

11. The non-transitory computer-readable storage medium of claim 9, wherein the image has a dynamic or a variable encoding, so that at least some pixels represent different ranges of bases in the genome.

12. The non-transitory computer-readable storage medium of claim 9, wherein the image-analysis technique comprises a pretrained neural network.

13. The non-transitory computer-readable storage medium of claim 9, wherein a given intensity corresponds to an expression level in a type of biological sequencing.

14. A method of diagnosing a condition, comprising:
receiving biological data from a biological sample;
transforming the biological data into a spatial representation, wherein the transformation is based at least in part on a predefined relationship between the biological data and corresponding spatial locations in a genome;
selectively normalizing the transformed data to obtain normalized transformed data, wherein the selective normalization comprises using a first normalization range for data having a first read count less than a threshold, the first read count being transformed into a first intensity, and using a second normalization range for data having a second read count greater than the threshold, the second read count being transformed into a second intensity;
converting the normalized transformed data into an output image, wherein a given pixel in the output image represents a predefined or predetermined range of bases in the genome;
analyzing the image using an image-analysis technique to determine a classification to detect a disease, a trait, a state, a prognosis, a response to treatment, and/or the recurrence of a disease; and
outputting an indication of a condition based on the determined classification.

15. The method of claim 14, further comprising:
receiving the biological sample;
isolating the biological data from the biological sample; and
sequencing the biological data from the biological sample.

16. The method of claim 14, wherein the biological sample comprises one of: blood, urine, tissue, stool, saliva, or cerebral spinal fluid.

17. The method of claim 14, wherein the biological data comprises one of: genomic data, transcriptomic data, proteomic data, epigenomic data, mitochondria data, microbiome data, electrical signals, or metabolic data.

18. The method of claim 14, wherein the condition comprises one of: a diagnosis, a disease state, or a genetic status.

19. The method of claim 14, wherein outputting further comprises displaying the indication on a display.

20. The method of claim 14, wherein the indication is one or more of: an audio indication, a visual indication, or a haptic indication.

* * * * *